United States Patent
Hanewinkel et al.

(10) Patent No.: US 8,226,407 B2
(45) Date of Patent: Jul. 24, 2012

(54) MANDIBULAR MANIPULATOR

(75) Inventors: William H. Hanewinkel, Salt Lake City, UT (US); Michael B. Gleeson, Salt Lake City, UT (US)

(73) Assignee: Kosmo Technologies, LLC, Salt Lake City, UT (US)

( * ) Notice: Subject to any disclaimer, the term of this patent is extended or adjusted under 35 U.S.C. 154(b) by 0 days.

(21) Appl. No.: 13/130,517

(22) PCT Filed: Jun. 24, 2010

(86) PCT No.: PCT/US2010/001839
§ 371 (c)(1),
(2), (4) Date: May 20, 2011

(87) PCT Pub. No.: WO2011/005299
PCT Pub. Date: Jan. 13, 2011

(65) Prior Publication Data
US 2011/0217674 A1    Sep. 8, 2011

Related U.S. Application Data

(60) Provisional application No. 61/269,344, filed on Jun. 24, 2009.

(51) Int. Cl.
*A61C 5/00* (2006.01)
(52) U.S. Cl. .......................................... 433/140; 433/69
(58) Field of Classification Search ................ 433/7, 27, 433/54, 55, 68, 69, 140, 149; 33/513, 514; 600/589, 590
See application file for complete search history.

(56) References Cited

U.S. PATENT DOCUMENTS

| | | | |
|---|---|---|---|
| 2,669,988 | A | 5/1951 | Carpenter |
| 4,148,308 | A | 4/1979 | Sayer |
| 4,283,173 | A | 8/1981 | Browne et al. |
| 4,425,911 | A | 1/1984 | Luomanen et al. |
| 4,439,147 | A | 3/1984 | Magill et al. |
| 4,472,140 | A | 9/1984 | Lustig |
| 4,495,945 | A | 1/1985 | Liegner |

(Continued)

FOREIGN PATENT DOCUMENTS

CA    2 189 174    10/1996
(Continued)

OTHER PUBLICATIONS

International Search Report PCT/US2010/001839 dated Mar. 31, 2011.

(Continued)

*Primary Examiner* — Cris L Rodriguez
*Assistant Examiner* — Matthew Saunders
(74) *Attorney, Agent, or Firm* — TraskBritt

(57) ABSTRACT

A mandibular manipulator instrument used as a standalone tool or with associated mouthpiece that includes two interlocking laterally sliding frames which interlock to create a movable upper and a lower incisor pull driven by a pair of pinion shafts and shaped for receiving a patient's central incisor teeth. A screw thread is used to provide a precise lateral motion for the sagittal measurement. The mouthpiece is constructed of resilient rubber. The mandibular manipulator may be positioned and held in a resilient flexible mouthpiece by the two pinions protruding through acoustically tight apertures respective to each pinion's position. The manipulator can be used for other application in an embodiment without the mouthpiece and/or in combination with a bite registration shape that is part of the manipulator frame.

15 Claims, 14 Drawing Sheets

U.S. PATENT DOCUMENTS

| | | | |
|---|---|---|---|
| 4,602,905 A * | 7/1986 | O'Keefe, III | 433/41 |
| D288,346 S | 2/1987 | Walsh | |
| 4,806,100 A | 2/1989 | Schainholz | |
| 4,827,943 A | 5/1989 | Bornn et al. | |
| 4,828,418 A | 5/1989 | Sauer et al. | |
| 4,901,737 A | 2/1990 | Toone | 128/848 |
| 5,024,218 A | 6/1991 | Ovassapian et al. | |
| 5,086,768 A | 2/1992 | Niemeyer | |
| 5,154,608 A * | 10/1992 | Feher | 433/57 |
| 5,154,609 A * | 10/1992 | George | 433/68 |
| 5,199,872 A | 4/1993 | Leal | |
| 5,280,791 A | 1/1994 | Lavie | |
| 5,305,741 A | 4/1994 | Moles | |
| 5,313,960 A | 5/1994 | Tomasi | 128/848 |
| 5,365,945 A | 11/1994 | Halstrom | 128/848 |
| 5,374,237 A * | 12/1994 | McCarty, Jr. | 601/38 |
| 5,409,017 A | 4/1995 | Lowe | |
| 5,427,117 A | 6/1995 | Thornton | 128/848 |
| 5,537,994 A | 7/1996 | Thornton | 128/204.18 |
| 5,566,683 A | 10/1996 | Thornton | 128/848 |
| 5,570,704 A | 11/1996 | Buzzard et al. | 128/848 |
| 5,611,355 A | 3/1997 | Hilsen | 128/848 |
| 5,642,737 A | 7/1997 | Parks | 128/848 |
| 5,678,567 A * | 10/1997 | Thornton et al. | 128/848 |
| 5,755,219 A | 5/1998 | Thornton | 128/201.18 |
| 5,794,627 A | 8/1998 | Frantz et al. | 128/848 |
| 5,816,799 A | 10/1998 | Parker | 433/6 |
| 5,823,193 A | 10/1998 | Singer et al. | 128/848 |
| 5,826,579 A | 10/1998 | Remmers et al. | |
| 5,846,212 A * | 12/1998 | Beeuwkes et al. | 601/38 |
| 5,868,138 A | 2/1999 | Halstrom | 128/848 |
| 5,884,628 A | 3/1999 | Hilsen | 128/848 |
| 5,921,942 A * | 7/1999 | Remmers et al. | 600/529 |
| 5,954,048 A | 9/1999 | Thornton | 128/201.18 |
| 5,983,892 A * | 11/1999 | Thornton | 128/201.26 |
| 6,041,784 A | 3/2000 | Halstrom | 128/848 |
| 6,055,986 A | 5/2000 | Meade | 128/848 |
| 6,109,265 A | 8/2000 | Frantz et al. | 128/848 |
| 6,155,262 A * | 12/2000 | Thornton et al. | 128/859 |
| 6,161,542 A | 12/2000 | Halstrom | 128/848 |
| 6,183,423 B1 | 2/2001 | Gaumond et al. | |
| 6,244,865 B1 * | 6/2001 | Nelson et al. | 433/140 |
| 6,273,859 B1 | 8/2001 | Remmers et al. | |
| 6,305,376 B1 | 10/2001 | Thornton | 128/848 |
| 6,325,064 B1 | 12/2001 | Thornton | 128/204.18 |
| 6,374,824 B1 | 4/2002 | Thornton | 128/201.26 |
| 6,379,311 B1 | 4/2002 | Gaumond et al. | |
| 6,516,805 B1 | 2/2003 | Thornton | 128/848 |
| 6,634,353 B1 | 10/2003 | Knebelman et al. | 128/200.24 |
| 6,729,335 B1 | 5/2004 | Halstrom | 128/848 |
| 6,769,910 B1 | 8/2004 | Pantino | 433/6 |
| 6,877,513 B2 | 4/2005 | Scarberry et al. | 128/848 |
| 7,146,982 B2 | 12/2006 | Mousselon et al. | 128/848 |
| 7,174,895 B2 | 2/2007 | Thornton et al. | 128/848 |
| 7,328,698 B2 * | 2/2008 | Scarberry et al. | 128/200.24 |
| 7,328,705 B2 | 2/2008 | Abramson | 128/848 |
| 7,331,349 B2 | 2/2008 | Brady et al. | 128/848 |
| 7,357,635 B2 | 4/2008 | Belfor et al. | 433/24 |
| 7,364,429 B2 | 4/2008 | Olivier | |
| 7,448,388 B2 * | 11/2008 | Halstrom | 128/861 |
| 7,832,403 B2 | 11/2010 | Halstrom et al. | |
| 2001/0047805 A1 | 12/2001 | Scarberry et al. | |
| 2005/0028827 A1 * | 2/2005 | Halstrom | 128/861 |
| 2005/0081859 A1 | 4/2005 | Scarberry et al. | 128/206 |
| 2005/0175954 A1 | 8/2005 | Zacher | 433/5 |
| 2007/0209666 A1 * | 9/2007 | Halstrom et al. | 128/859 |
| 2007/0264609 A1 * | 11/2007 | Brunner et al. | 433/69 |
| 2008/0105268 A1 | 5/2008 | Kusukawa | |
| 2010/0316973 A1 | 12/2010 | Remmers et al. | |

FOREIGN PATENT DOCUMENTS

| | | |
|---|---|---|
| CA | 2 236 456 | 10/1996 |
| EP | 1 832 306 | 9/2007 |
| WO | 97/16151 | 5/1997 |
| WO | 0152928 | 7/2001 |
| WO | 03092562 | 11/2003 |
| WO | 2006/070805 | 7/2006 |
| WO | 2011005299 A2 | 1/2011 |

OTHER PUBLICATIONS

Written Opinion PCT/US2010/001839 dated Mar. 31, 2011.

* cited by examiner

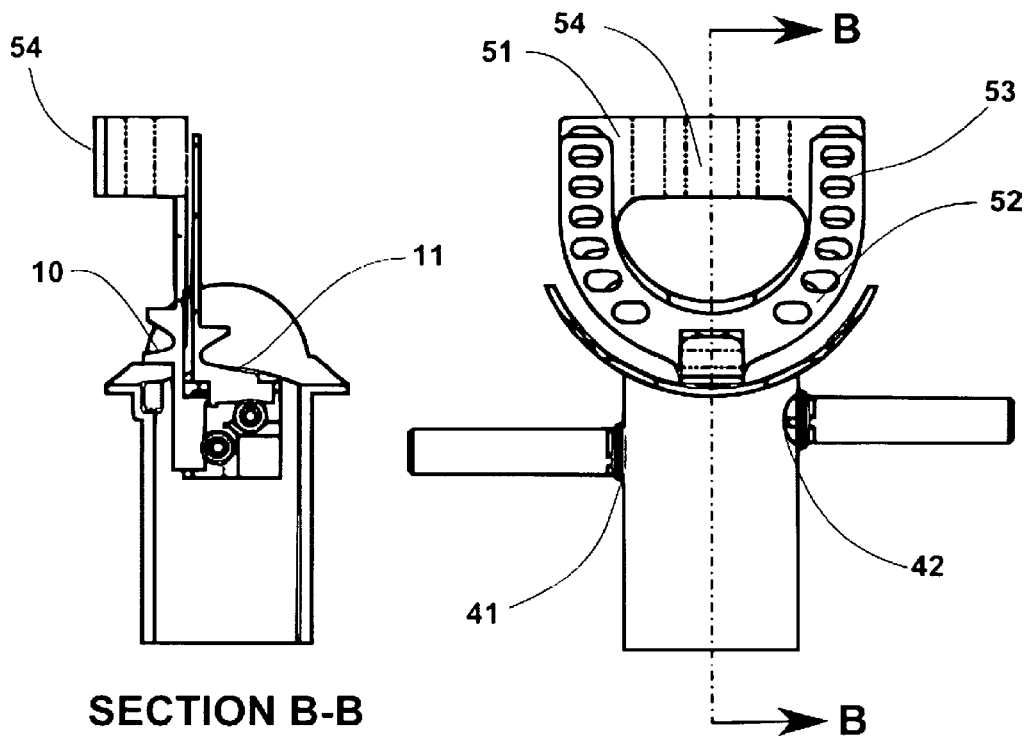
SECTION B-B
FIG. 7
FIG. 6
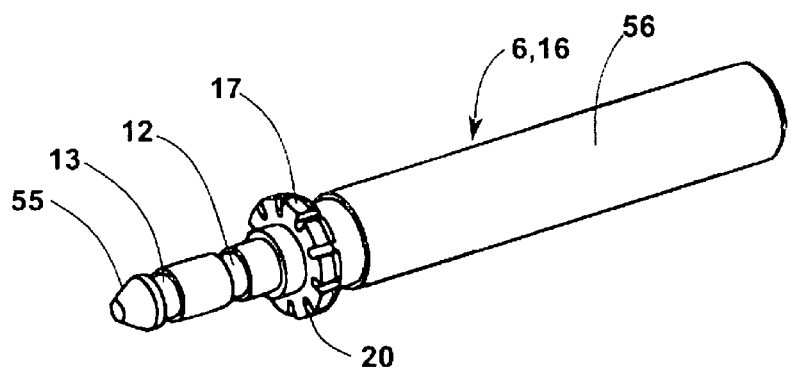
FIG. 8

MANDIBULAR MANIPULATOR

CROSS-REFERENCE TO RELATED APPLICATION

This application claims priority under Article 8 of the Patent Cooperation Treaty and 35 U.S.C. §119(e) to U.S. Provisional Application Ser. No. 61/269,344, filed on Jun. 24, 2009, the contents of which are incorporated herein by this reference.

TECHNICAL FIELD

This invention relates generally to medical and dental equipment, and more particularly relates to an instrument and associated methods used as an adjunct to instruments for diagnosing dental and medical problems associated with a patient's mandibular (jaw) position and requiring the accurate measuring of the mandible relative to the maxilla in three orthogonal dimensions.

BACKGROUND

The current state of the art for manipulating a patient's mandible includes the well-known George Gauge™. (See, for example, U.S. Pat. No. 7,448,388.) The George Gauge™ allows for the movement of the lower mandible only in the anteroposterior axis and minimal vertical change.

Several problems can occur with the current method of achieving desired mandibular position because the patient is instructed to, e.g., position their mandible as the dental/medical procedure is performed. In several instances, the current methodology is tried sequentially in set intervals while having to remove the instrument between setting of the mandible and recording the patients bite registration. Present methods lack the precision and repeatability needed to analyze a patient in real time with any diagnostic instrument or during other dental procedures requiring mandibular manipulation. This trial and error method not only increases diagnosis time, but prevents an accurate means of noting where the relative position of the mandible lies in relation to the maxilla. Consequently, a dental appliance created for the patient can sometimes need to be re-created several times before the appliance works correctly. And, in some cases, the patient becomes dissatisfied with the overall lack of good results and gives up.

A U.S. patent search was conducted, and the following patents (the contents of each of which are incorporated herein by this reference) were uncovered: U.S. Pat. No. 7,448,388 (Nov. 11, 2008) to Halstrom; U.S. Pat. No. 6,183,423 (Feb. 6, 2001) to Gaumond et al.; U.S. Pat. No. 6,379,311 (Apr. 30, 2002) to Gaumond et al.; U.S. Pat. No. 6,244,865 (Jun. 12, 2001) to Nelson et al.; U.S. Pat. No. 2,669,988 (May 8, 1951) to Carpenter; U.S. Pat. No. 4,148,308 (Apr. 10, 1979) to Sayer; U.S. Pat. No. 4,425,911 (Jan. 17, 1984) to Luomanen et al.; U.S. Pat. No. 4,495,945 (Jan. 29, 1985) to Liegner; U.S. Pat. No. 5,024,218 (Jun. 18, 1991) to Ovassapian et al.; U.S. Pat. No. 5,086,768 (Feb. 11, 1992) to Niemeyer; U.S. Pat. D288,346 (Feb. 17, 1987) to Walsh; U.S. Pat. No. 5,305,741 (Apr. 26, 1994) to Moles; U.S. Pat. No. 4,828,418 (May 9, 1989) to Sauer et al.; U.S. Pat. No. 4,472,140 (Sep. 18, 1984) to Lustig; U.S. Pat. No. 4,806,100 (Feb. 21, 1989) to Schainholz; U.S. Pat. No. 7,364,429 (Apr. 29, 2008) to Olivier; U.S. Pat. No. 5,154,609 (Oct. 13, 1992) to George; U.S. Pat. No. 5,199,872 (Apr. 6, 1993) to Leal; and U.S. Pat. No. 4,439,147 (Apr. 17, 1984) to Magill and Key.

SUMMARY OF THE INVENTION

Described are instruments used to diagnose and treat dental and medical problems associated with a patient's mandible positioning, wherein such diagnosis and treatment can beneficially utilize the accurate measurement of the subject's mandible relative to the maxilla in three dimensions. Such instruments have mechanical features for engaging the incisor teeth of the maxilla and mandible, a mechanical connection between the mandible and maxilla engagement means, and calibrations or other indicia provided on the mechanical connection for measuring relationships between the mandible and maxilla.

The mechanical connection between the mandible and maxilla engagement allows for a means of two self-retaining sliding incisor pulls that move perpendicular to one another and three rotating members to actuate the sliding incisor pulls. The sliding incisor pulls have a self-retaining shape and also have a small protrusion at one end so as to prevent their leaving the guide slots once a device according to the invention is assembled for use. The mechanical connection allows for motion of the incisor sliding pulls in both an anterior/posterior direction and a vertical direction and a third mechanical connection is provided to allow sagittal or right and left relative motion of the incisor pulls. A locking means is provided for the anterior/posterior motion and the vertical motion to allow the ideal position to be held. The sagittal position may be held by means of a thread/nut mechanism utilized for its positioning.

The instrument can either be utilized with or without a bite plate. When it is used with an impression plate, the plate has upper and lower planar surfaces for holding imprint materials, and the shape of the plate approximates the bite of the upper and lower teeth. Within this embodiment, the impression plate can be of different sizes and either be integral specifically to the sliding incisor pulls or be attached to the upper incisor pull by a retained "snap" feature or by other mechanical means to prevent its unintentional removal.

A threaded type of locking mechanism may be provided for the anteroposterior and the vertical motions and is used to fix the upper and lower incisor pulls in place.

Graduated scales or gradation markings or indicators are marked in the connecting frame of the instrument to accurately quantify the movement in both the anteroposterior, vertical axes as well as the sagittal movement. In another refined embodiment, the instrument allows for electronic feedback of the positions to be recorded by data logger or other computer recording, thus allowing for an automatic record of the mandible position.

Uses of this instrument can be applied to the diagnosis, treatment, or troubleshooting associated with, e.g., the causes of sleep apnea, temporomandibular joint dysfunction (TMD), problems associated with the Temporomandibular joints (TMJ), or any concern related to the alignment of the mandible in relationship to the maxilla. Another application of this instrument is for a qualitative measurement using bite registry material when performing a dental procedure or medical procedure requiring an accurate relationship of the position of the subject's mandible in relation to the maxilla.

Another embodiment is the use of remote movement of the instrument to achieve appropriate positioning of the mandible to open the airway in designing an oral appliance for a patient suffering from obstructive sleep apnea.

In yet another embodiment, the position of the mandible relative to the maxilla can be precisely measured or positioned while using electrodiagnostic equipment or radiology to realize the necessary location of the mandible, for creating a remedy for patients suffering from TMJ.

One use of the invention is in the application of an acoustic oral pharyngometer instrument to measure the area and volume of the throat opening of a patient as he or she breathes.

The simple motion of moving the lower mandible either anteroposterior and up and down, can help open the throat and ease the subject's breathing. The outcome of the procedure is to either create a dental appliance to use while the subject sleeps or for referral to another medical professional for further analysis of the patient's throat. Typically, a dental appliance is constructed from the resulting oral pharyngometer procedure and this is used to hold the mandible in a set position as the patient sleeps to prevent breathing difficulties. The invention allows the oral pharyngometer procedure to be performed in "real time" without having to sequentially remove the adjusting instrument.

The acoustic pharyngometer sees the mandibular manipulator described herein as an object in the airway waveguide prior to the acoustic wave entering the patient's mouth and throat, but does not attenuate the overall strength of the returning signal. Because the overall mouthpiece tube is longer in length, the anteroposterior distances are shifted the same distance in the pharyngometer readout but the relative distances of the incisors to the soft pallet and pharyngeal remain constant.

Another embodiment is the use of remote movement of the instrument to achieve appropriate positioning of the mandible to open the airway in designing an oral appliance for a patient suffering from obstructive sleep apnea.

In yet another embodiment, the position of the mandible relative to the maxilla can be precisely measured or positioned while using, e.g., electrodiagnostic equipment or radiology equipment, to realize the necessary/preferred location of the subject's mandible, for creating a remedy for patients suffering from, e.g., TMJ.

It would be beneficial to, e.g., dentists and sleep apnea physicians to utilize an instrument that quantifies in a reliable, repeatable, and easy way, the relative position of the subject's mandible to the maxilla for real time measurement in three planes from the most posterior to the most anterior and from the least vertical to the maximum vertical position paths, and from the sagittal centerline both left and right.

In a preferred embodiment, the instrument (e.g., a mandibular manipulator) operates by inserting a snorkel-like mouthpiece into a patient's mouth and engaging the patient's upper and lower front teeth with the upper and lower manipulator incisor pulls. For instance, an acoustic pharyngometer or other medical instrument may be attached to the open end of the mouthpiece and operated therein per the manufacturer's instructions. The mandibular manipulator is operated by rotation of the pinions either by hand, small electric or pneumatic motors by computer feedback, or the like with the pharyngometer or medical instrument. The patient's mandible may then be manipulated by the two lifts until the mandible position is such that the ideal airway is shown by the medical instrument readout. The dentist may at this point apply a quick setting bite paste to provide an impression for the creation of a dental appliance.

Methods of making and using the device are also disclosed herein.

DESCRIPTION OF THE DRAWINGS

FIG. 6 is a top view of a device according to the invention.

FIG. 7 is a cross-sectional view B-B of FIG. 6.

FIG. 8 is a perspective view of the pinion element.

MODE(S) FOR CARRYING OUT THE INVENTION

The following terminology is used herein:

Dental Articulator Mechanical instruments that simulate the temporomandibular joints and jaws to which maxillary and mandibular casts are attached. The entire assembly attempts to reproduce the movements of the mandible and the various tooth-to-tooth relationships that accompany those movements.

Maxilla: anatomy; of a pair of bones of the human skull fusing in the mid line and forming the upper jaw.

Dental: The irregularly shaped bone forming half of the upper jaw. The upper jaw is made up of the two maxillae.

Incisal edges of the lower to upper central incisor teeth.

Anteroposterior: Anatomical term referring to an axis and for the purpose of this application defines an axis from front to back of the mouth.

Sagittal: A vertical plane passing through the standing body from front to back.

Figure 1:
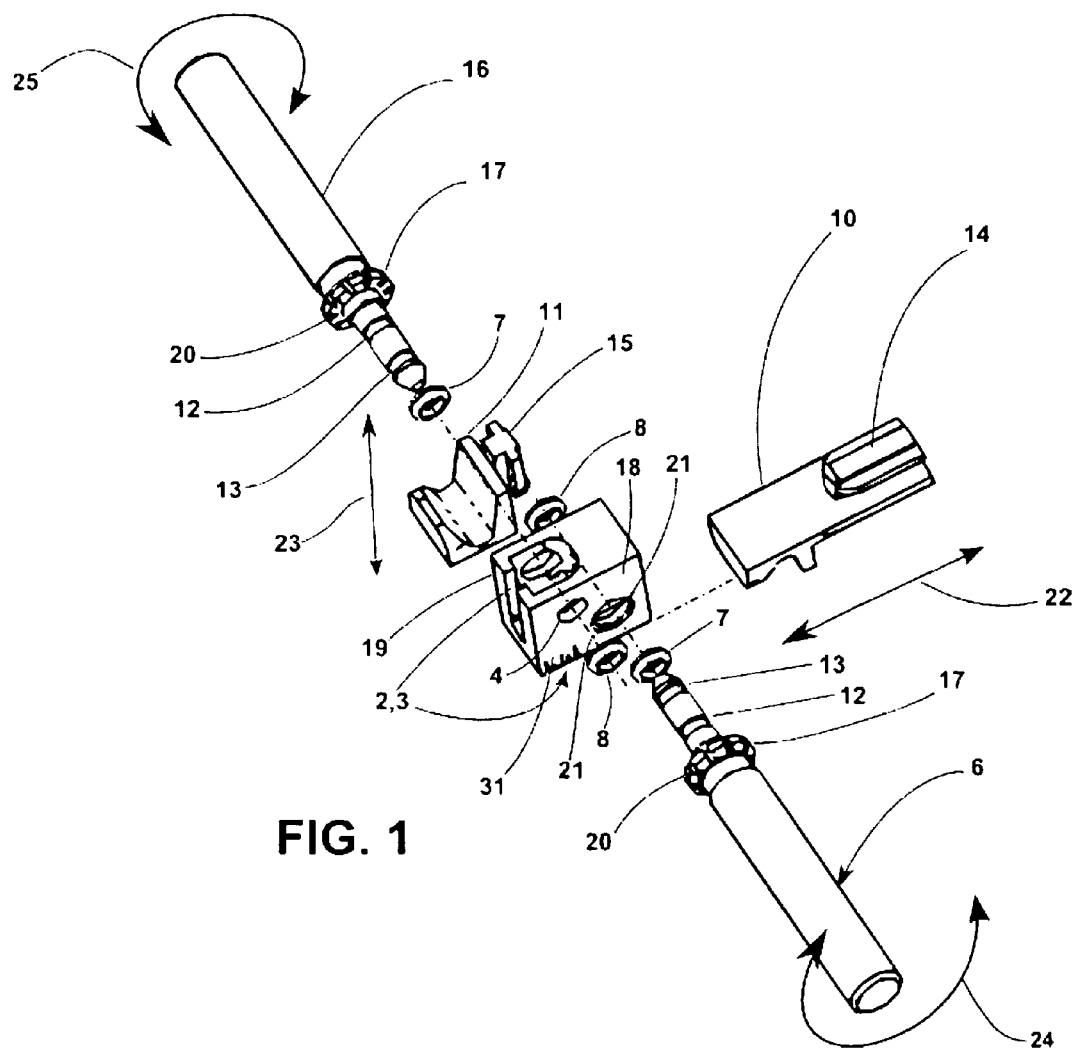
FIG. 1 is an exploded view of a device according to the invention without the mouthpiece or bite register.
Figure 2:
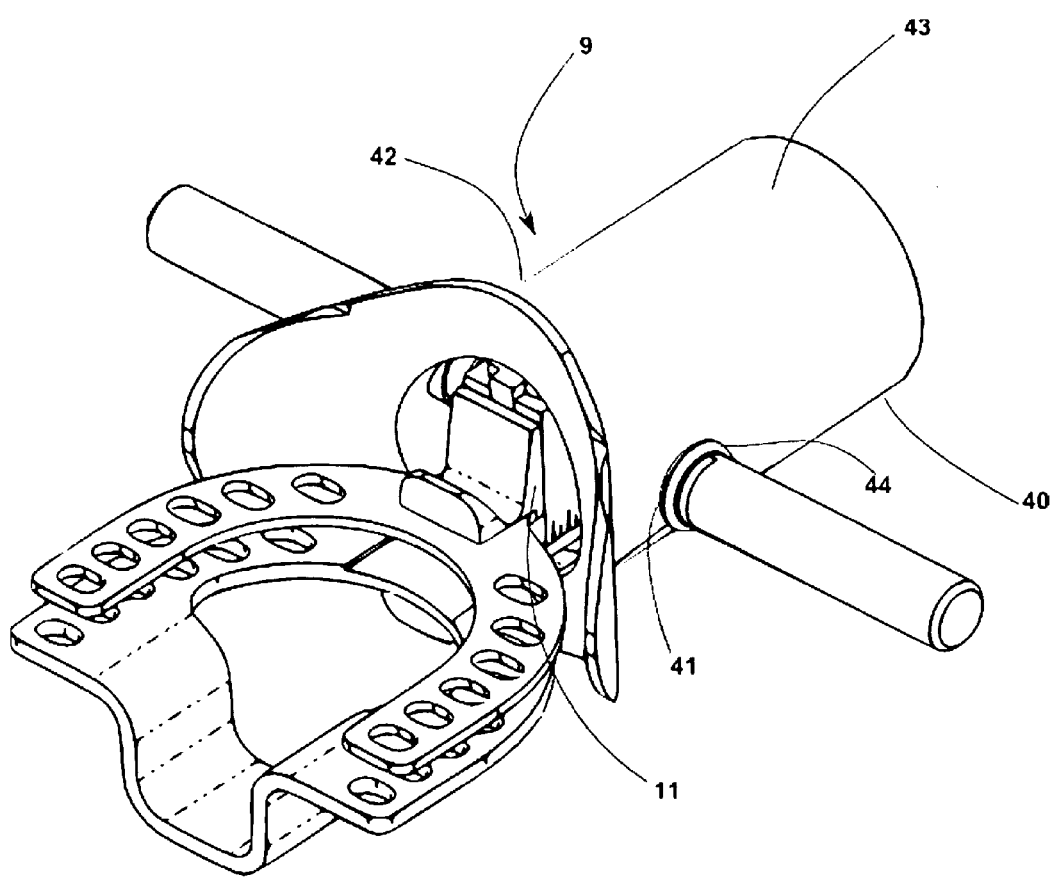
FIG. 2 is a perspective view of the manipulator assembly in its entirety with mouthpiece.
Figure 3:
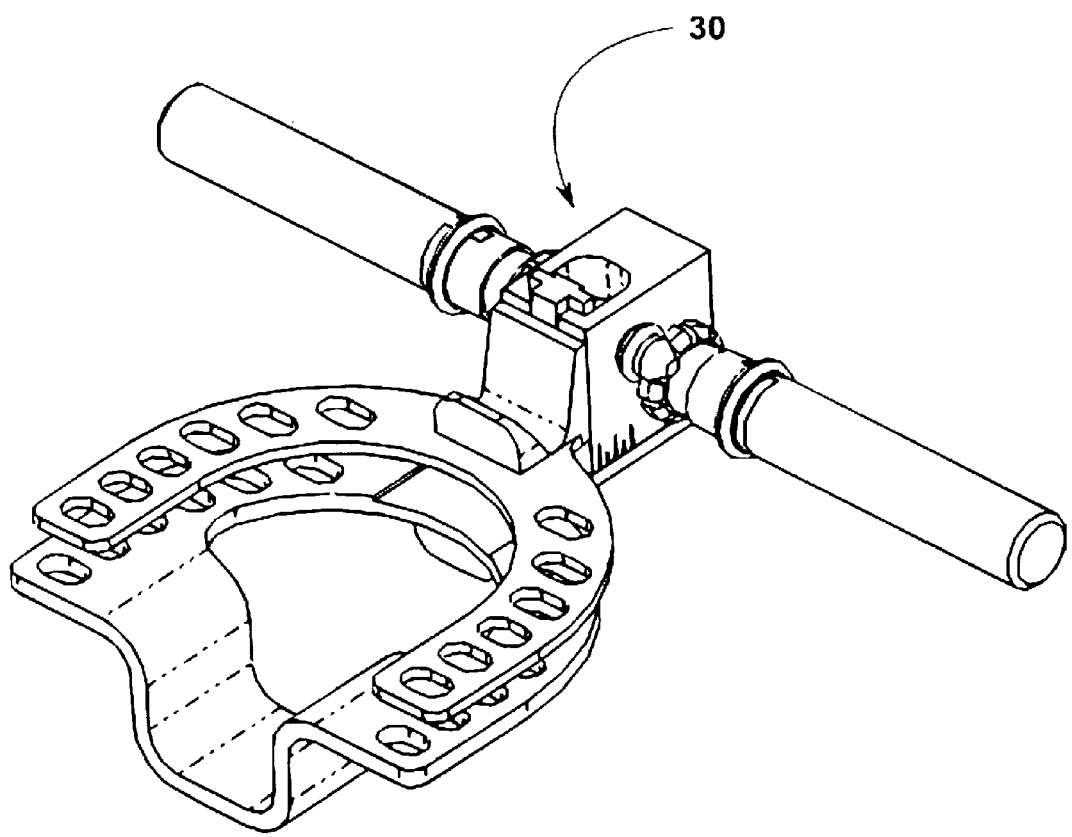
FIG. 3 is a perspective view of the manipulator with bite registers and without the mouthpiece.
Figure 4:
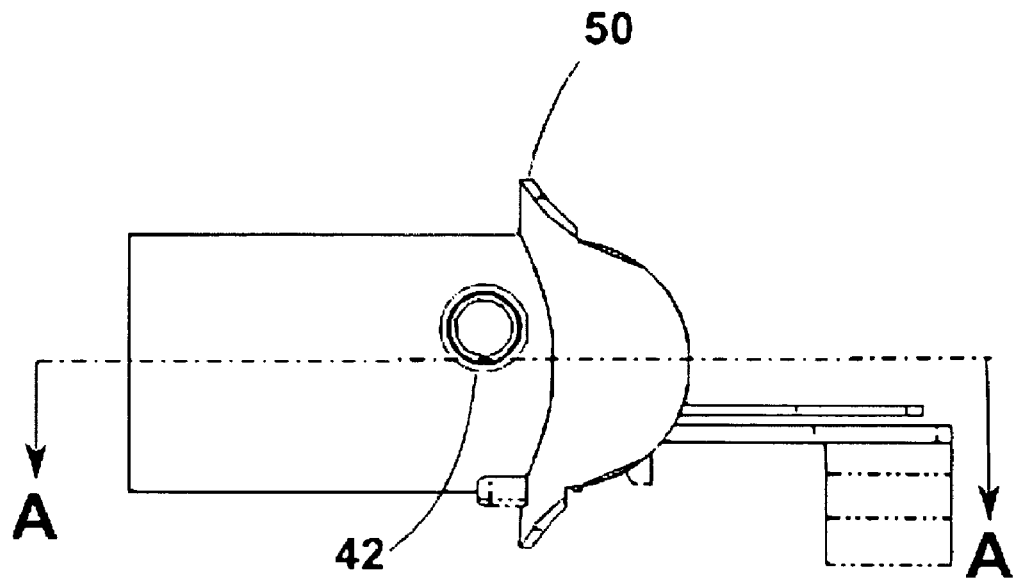
FIG. 4 is a left side view of a device according to the invention.
Figure 5:
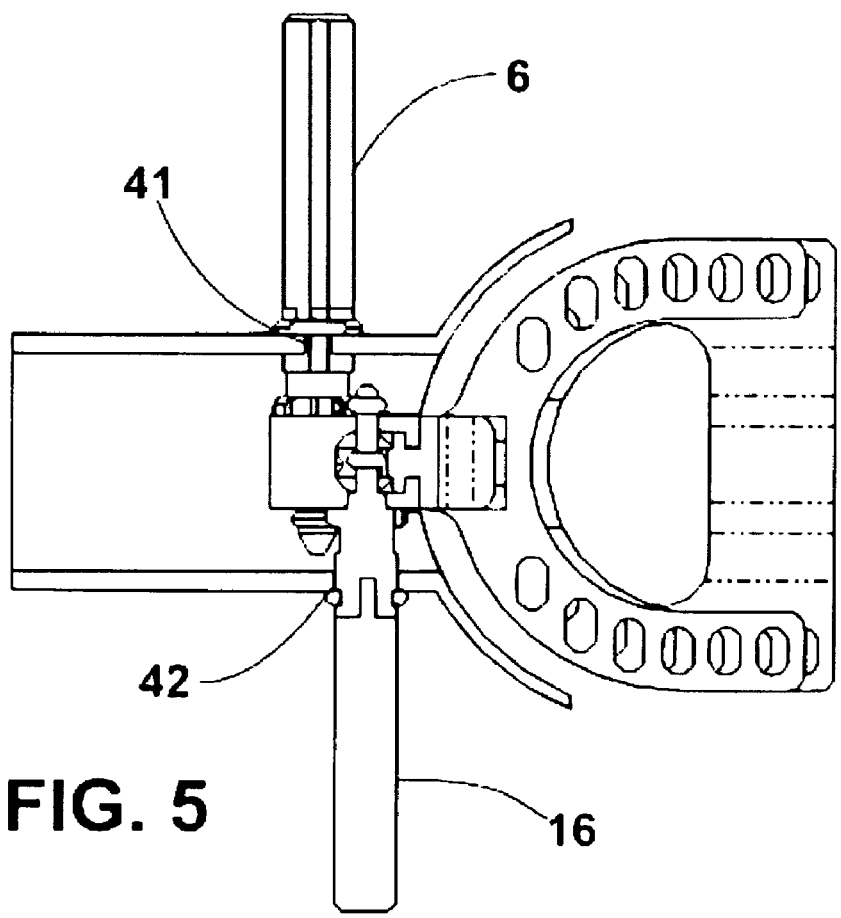
FIG. 5 is a cross-sectional view A-A of FIG. 4.

With reference now to FIGS. 1, 2, and 3, arrow 9 shows the overall mandibular manipulator as a self-contained unit for measurement in the anteroposterior and vertical movements of a patient's mandible in relation to the maxilla. The manipulator assembly begins with a frame 1 having slots 2, 3 and aligned holes, e.g., 4. Pinions 6, 16 are assembled through the holes while adding O-rings 7, 8. In this embodiment, lower incisor pull 10 and upper incisor pull 11 engage and are received by slots 2, 3 and slide in directions shown by arrows 22, 23, respectively.

Figure 11:
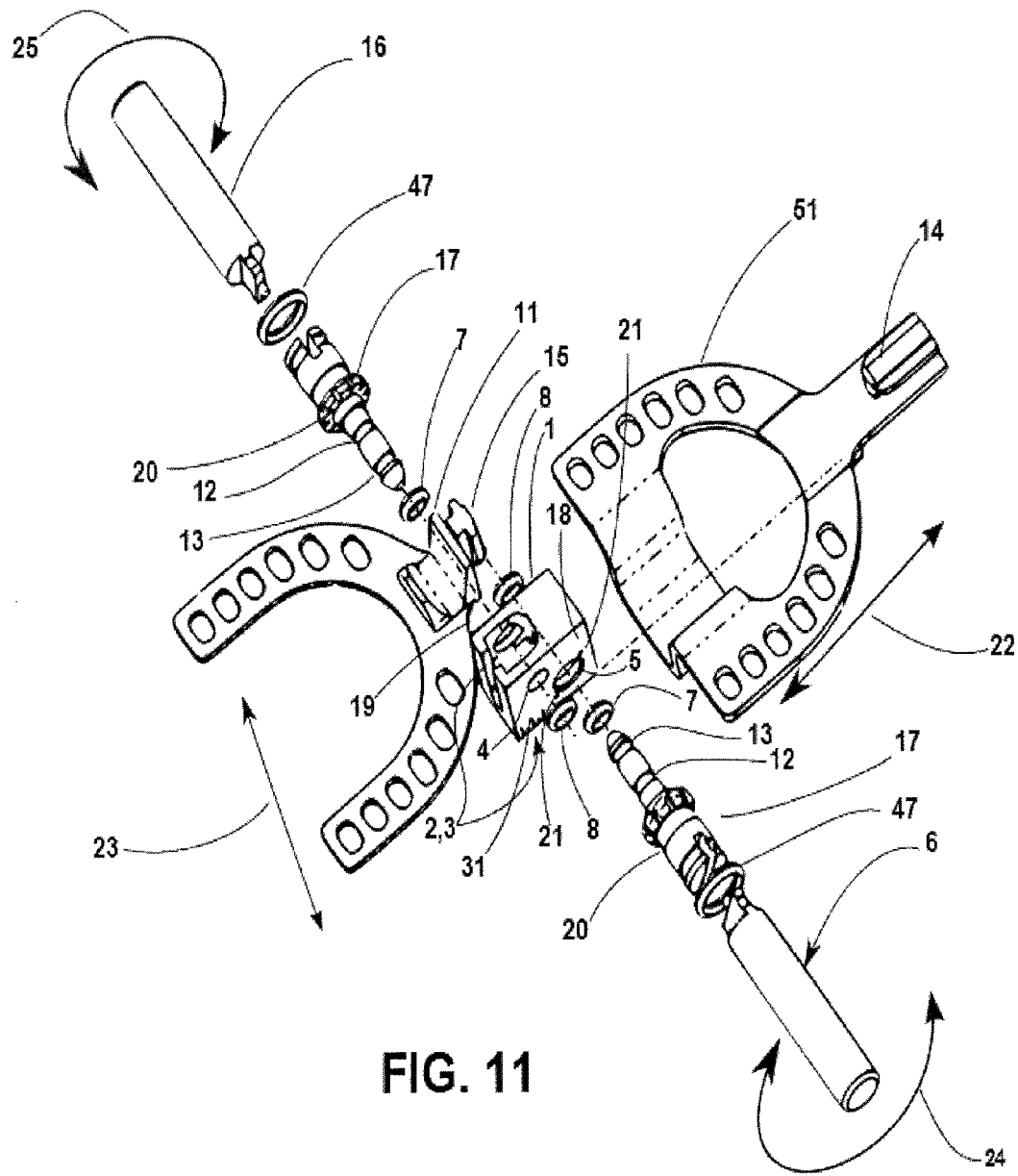
FIG. 11 is an exploded view of a device according to the invention without the mouthpiece while including an integrated bite register.

O-rings 7, 8 serve different functions. O-ring 7 seats on groove 12 and is squeezed against protruding surfaces 14 and 15 of incisor pulls 10 and 11, respectively. When pinion 6 or 16 are rotated in directions 24 or 25, there is a translation of rotational to linear motion by the friction of O-ring 7 against the incisor pulls 10 and 11, respectively. A small rack and pinion gear set, or other such device could also take the place of O-ring 7 and protruding surfaces 14, 15 to create a means for the translation of motion. The rack and pinion gear sets, 77 are utilized in the embodiment described in FIG. 16 through 21. O-rings 8 or another ring of resilient form are used to retain pinions 6, 16 within the frame 1 when seated in groove 13. Additionally, O-ring 8 creates an axial bias to the pinions 6, 16. This bias action is used to pull the pinions' 6, 16 flange 17 toward the frame side 18, 19 (19 is the surface opposite 18). Radial slots 20 equally spaced around flange 17 engage protrusions 21 (typical to opposite side of frame for aligned hole 4) to create a soft detent. This detent creates a tactile feedback when the pinion 6, 16 is rotated by hand to offer the operator a measurement of how far incisor pulls 10, 11 have moved relative to rotation shown by arrows 24, 25. O-ring 47 (shown in FIG. 11) creates a seal between the flange 17 member and the pinion 6, 16 members. A dial or other visual indicator rigidly part of pinion 6, 16 could also be used to indicate distance traveled by incisor pulls 10, 11. Gradation indicators 31 shown in FIG. 1 on frame 1 are used to clearly indicate and measure travel of the pull 10.

In more detail now to FIGS. 2 and 3, the assembled mechanism of FIG. 1, now shown with the bite plate pulls, and shown in FIG. 3 by arrow 30 is assembled within Mouthpiece 40. Holes 41 and 42 provide a fit that is tight enough around pinions 6, 16 to create acoustic seal 44. The round cylindrical tube 43 of mouthpiece 40 creates an airway and can be attached to a medical instrument, for instance, an acoustic oral pharyngometer.

Referring now to FIGS. 4, 5, 6, 7, and 15, the mouthpiece 40 is made of resilient material and fits into a patient's mouth similar to a snorkel mouthpiece. Surface of Flange 50 sets within the inner surface of a patient's lips while the incisor pulls 10, 11 engage the patients front teeth. Upper and lower surfaces of bites 51, 52 are contacted by the patient's molars and incisor teeth. Bites 51, 52 feature through holes 53 provided to hold bite registration paste that would be injected into these areas by a Physician or Dentist. Tongue depressor 54 formed on bite 51 is used to keep the patient's tongue from interfering with the medical measurement. Tongue depressor 54 is shown also in FIG. 15.

In more detail now to FIG. 8, a perspective view of pinion 6, 16 is shown for communicating in more detail. Conical surface 55 is a feature of the pinion to allow the O-rings 7, 8 to be assembled more easily into grooves 12, 13. Cylindrical surface 56 can have various surface textures applied. One embodiment would be a straight or diamond knurl pattern for instance so as to provide an improved finger grip to the pinion. In yet another embodiment, a soft, resilient tubing such as silicone or latex could slip over surface 56 for the same purpose of providing an improved grip. Cylindrical surface 56 could also be attached to a small servo motor mechanism to drive pinion 6, 16 with a feedback surface to the medical instrument being used. In this way, the entire medical measurement is computer driven and the mandible position is optimized.

Figure 9:
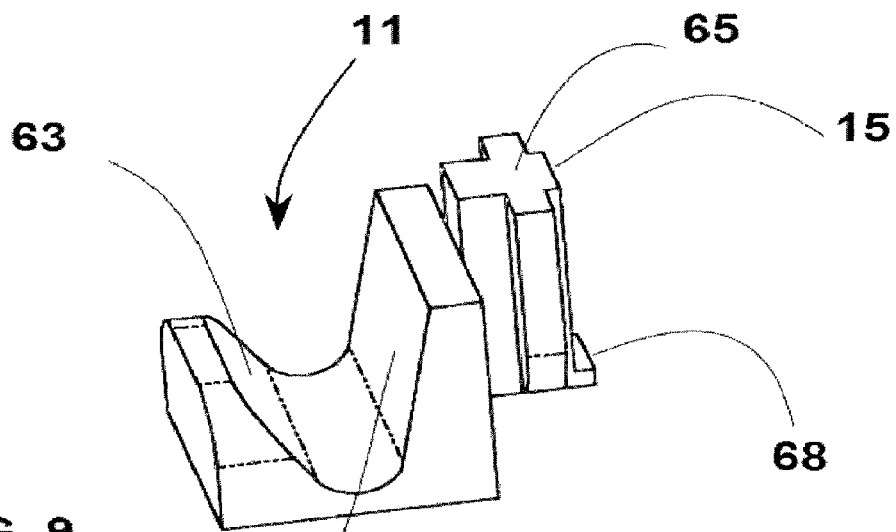
FIG. 9 is a perspective view of the upper incisor pull.
Figure 10:
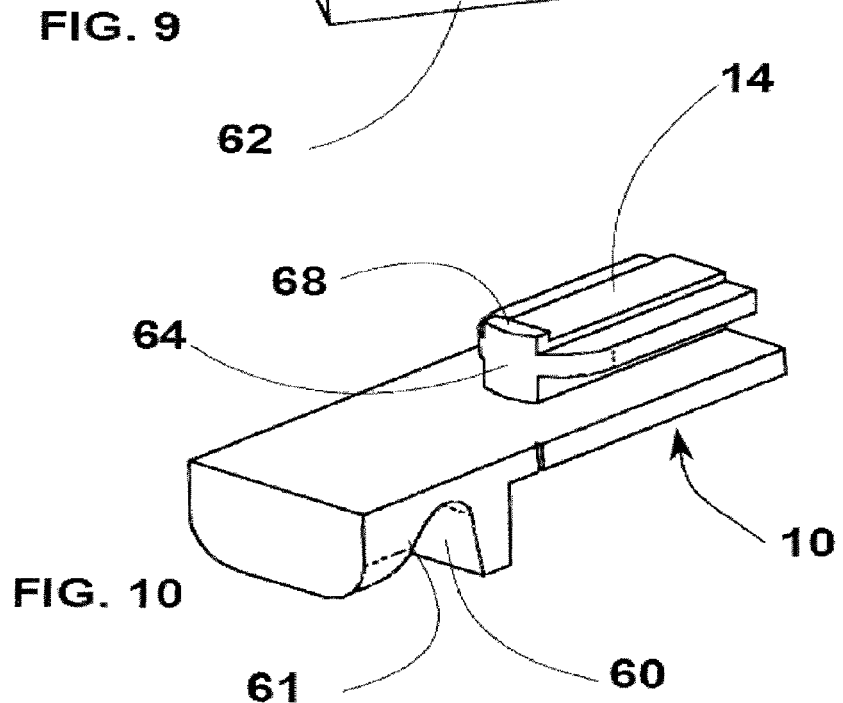
FIG. 10 is a perspective view of the lower incisor pull.

In more detail now to FIGS. 9 and 10, are the upper incisor pull 11 and lower incisor pull 10, respectively. Both incisor pulls 10, 11 use similar angled walls 60, 61, 62, and 63 to engage and receive the patients incisors. In another embodiment, these walls could be rounded and reshaped to engage more of the patient's upper and lower teeth surfaces. Both incisor pulls 10 and 11 have similar sliding "T" shaped slides 64 and 65. These guides self-capture in slots 2, 3 of the frame 1. While this is one embodiment of a captured sliding guide, another example would be a dovetail or some similar mechanical capturing slide mechanism. Incisor pulls 10, 11 have stop features 68 to prevent the incisor pulls 10, 11 from coming free of the frame. Incisor pulls 10, 11 also feature protruding surfaces 14 and 15 which allow for both adjustment of the O-ring 7 pressure and provide a roughened surface to provide more friction to the O-ring. In another embodiment, protruding surfaces 14 and 15 could be gear rack teeth which would engage mating gear teeth on pinion 6, 16 in place of O-ring 7. Other types of translation from rotational to linear motion could be used in this application.

Figure 12:
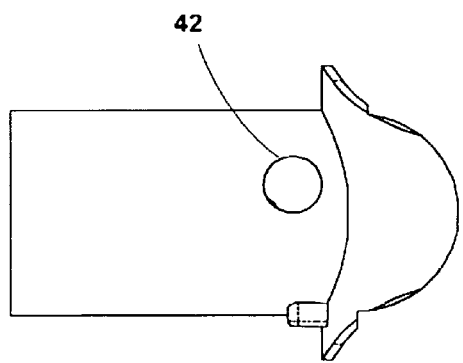
FIG. 12 is a side view of the mouthpiece.
Figure 13:
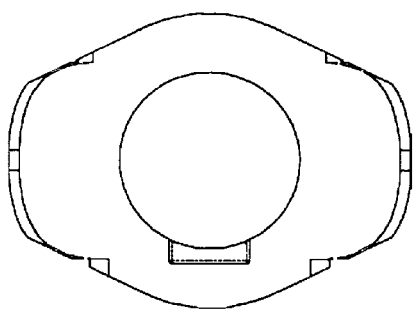
FIG. 13 is a rear view of the mouthpiece.
Figure 14:
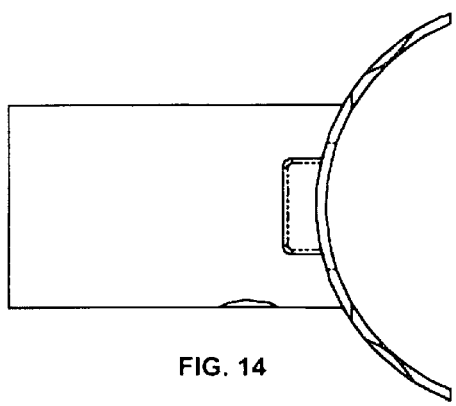
FIG. 14 is a bottom view of the mouthpiece.
Figure 15:
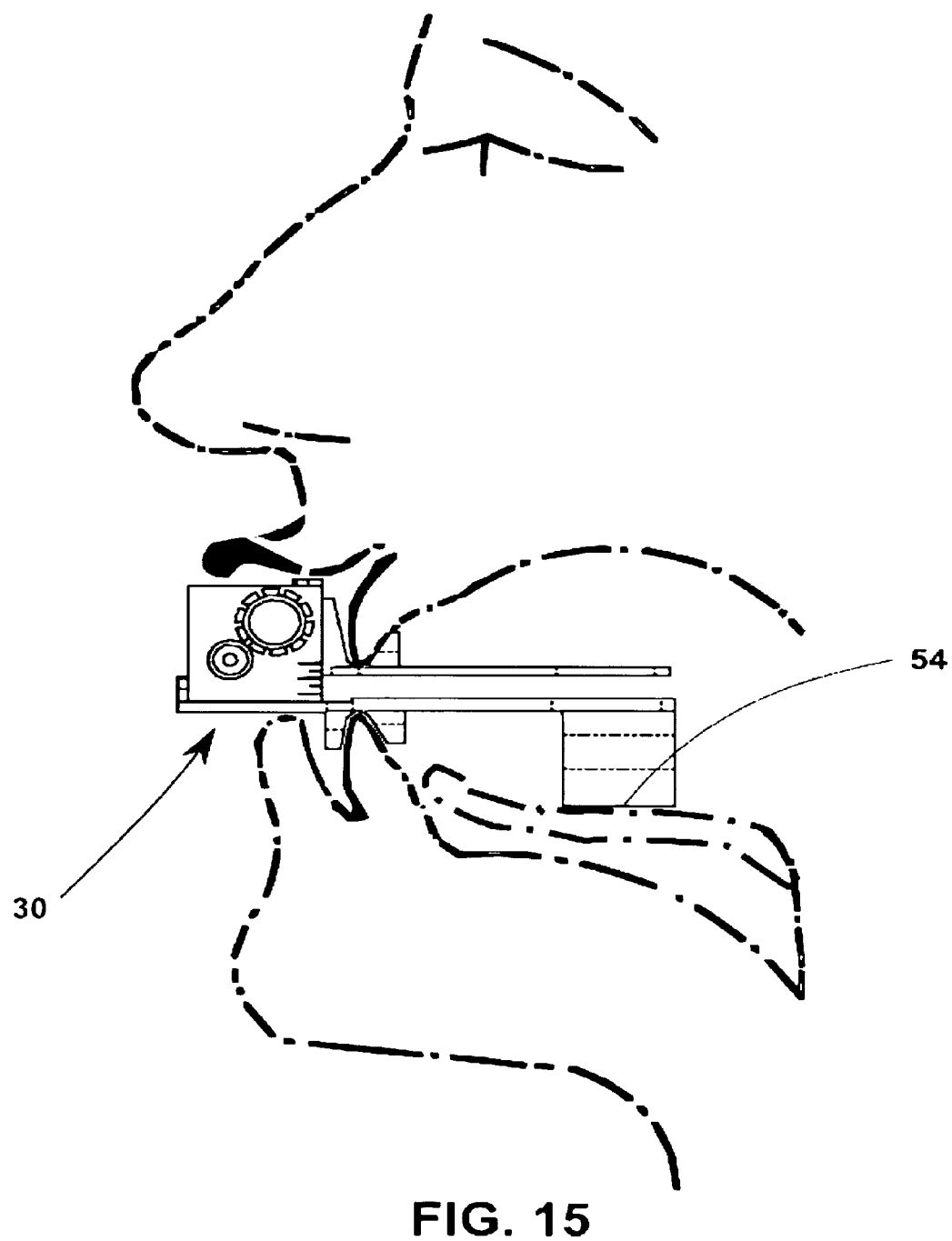
FIG. 15 is a cross-sectional side view of the lateral maxilla and mandible with the invention that includes the integrated bite register.

FIGS. 12, 13, and 14 are orthographic views of the mouthpiece 40.

Figure 16:
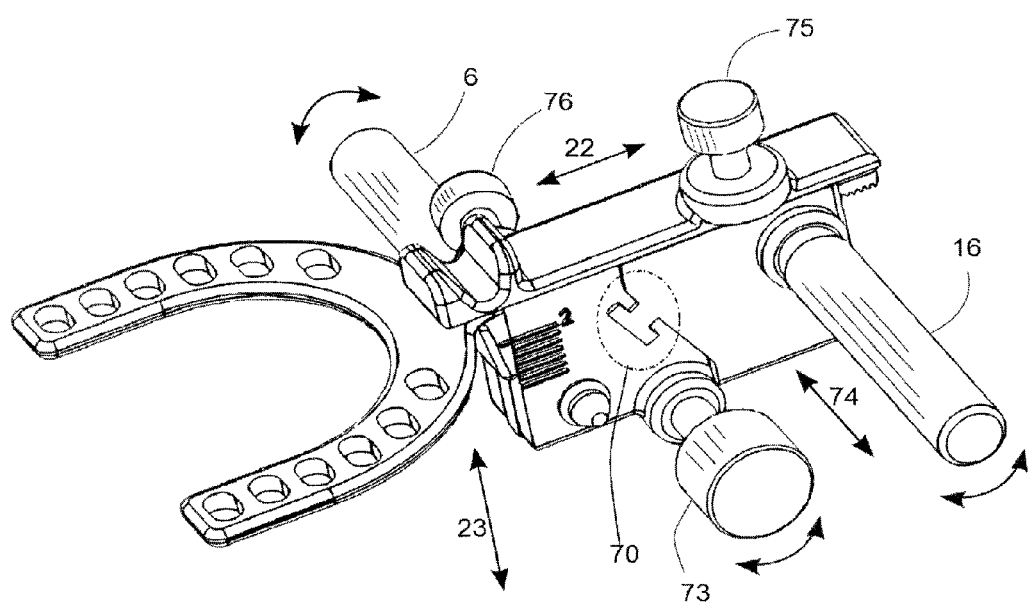
FIG. 16 is a perspective view of the embodiment which allows for the measurement of the mandible relative to the maxilla in three dimensions.

Another embodiment of the invention allows for the measurement of the mandible relative to the maxilla in three dimensions. FIG. 16 shows a detailed perspective view in which an additional sliding joint 70 is added to the instrument to provide for the patient's mandible measurement in the sagittal direction. This embodiment would be applied to the patient as described in FIG. 15. In this instance, frame 1 is now two parts 71, 72 while each carries the slots 2, 3 and corresponding aligned holes 4, 5 respectively. Frame parts 71, 72 interact and attach to one another through joint 70. Joint 70 forms the sagittal axis of movement. The sagittal movement, described by arrow 74, is accomplished by adjusting element 73. Incisor pulls 10, 11 with incisor pull 11 having an arched bite configuration as described earlier, move in the same manner as described per FIG. 1.

Figure 17:
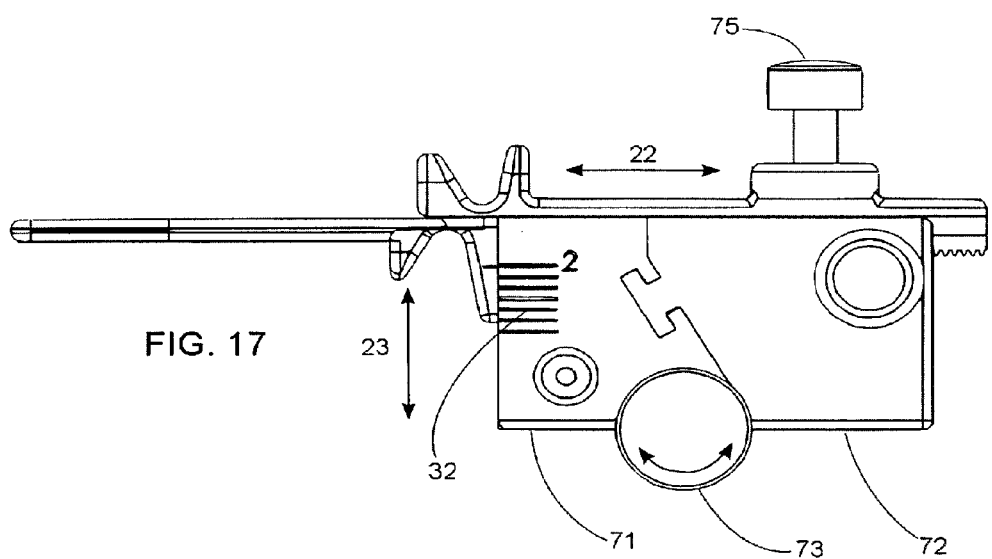
FIG. 17 is a right view of the embodiment of FIG. 16.
Figure 19:
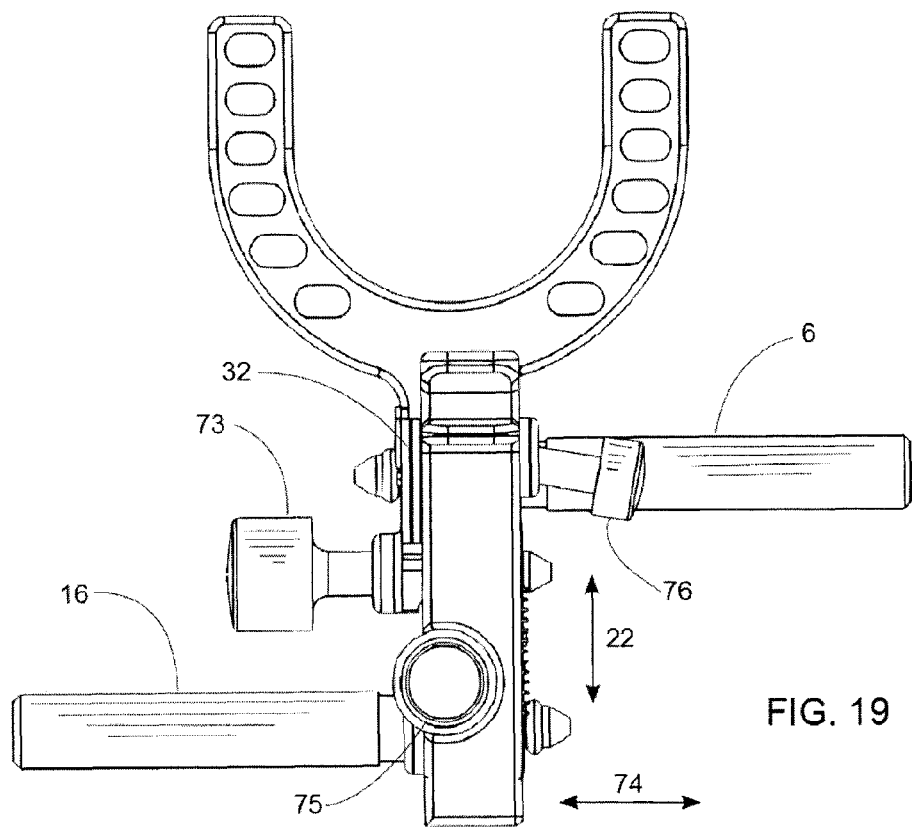
FIG. 19 is a top view of the embodiment of FIG. 16.
Figure 20:
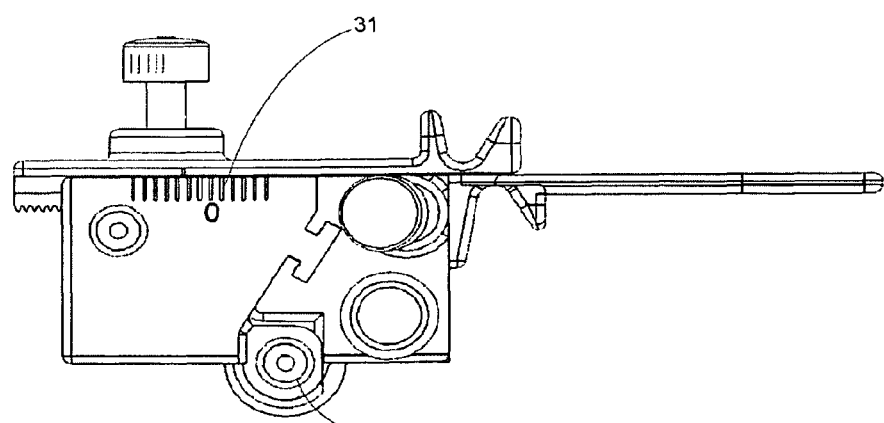
FIG. 20 is a left side view of the embodiment of FIG. 16.

FIGS. 17, 19, and 20 show indicia, such as, gradation indicators 31 and 32, accurately describing the movement for each axis of the instrument. In the depicted embodiment, once the instrument has been adjusted for the ideal position for the patient, motions 22 and 23 are locked using fixation members 75, 76. FIG. 17 shows gradation indicators 32 with the normal occlusion starting point of, e.g., about two mm represented by the numeral 2 in the figure. FIG. 20 shows the gradation indicators 31 with the numeral 0 representing the normal occlusion location.

Figure 18:
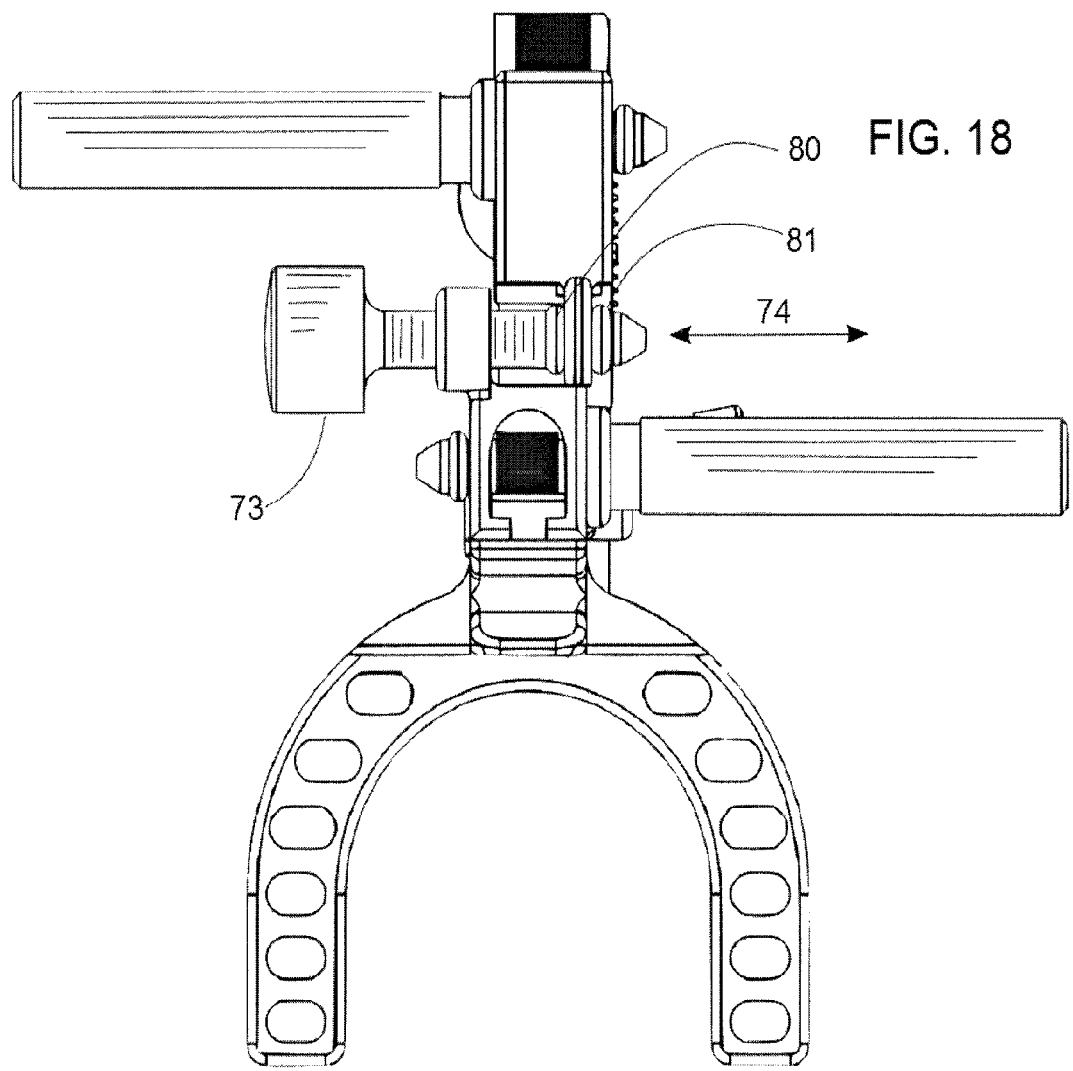
FIG. 18 is a bottom view of FIG. 17.

Referring to FIG. 18, the sagittal slide joint 70 allows frame blocks 71, 72 to move relative to one another by adjusting screw element 73. Adjusting screw element 73 is threaded into hole 78 in frame block 71 and then attached to frame block 72 through hole 79 and retained with two resilient rings or O-rings, 80, 81.

Figure 21:
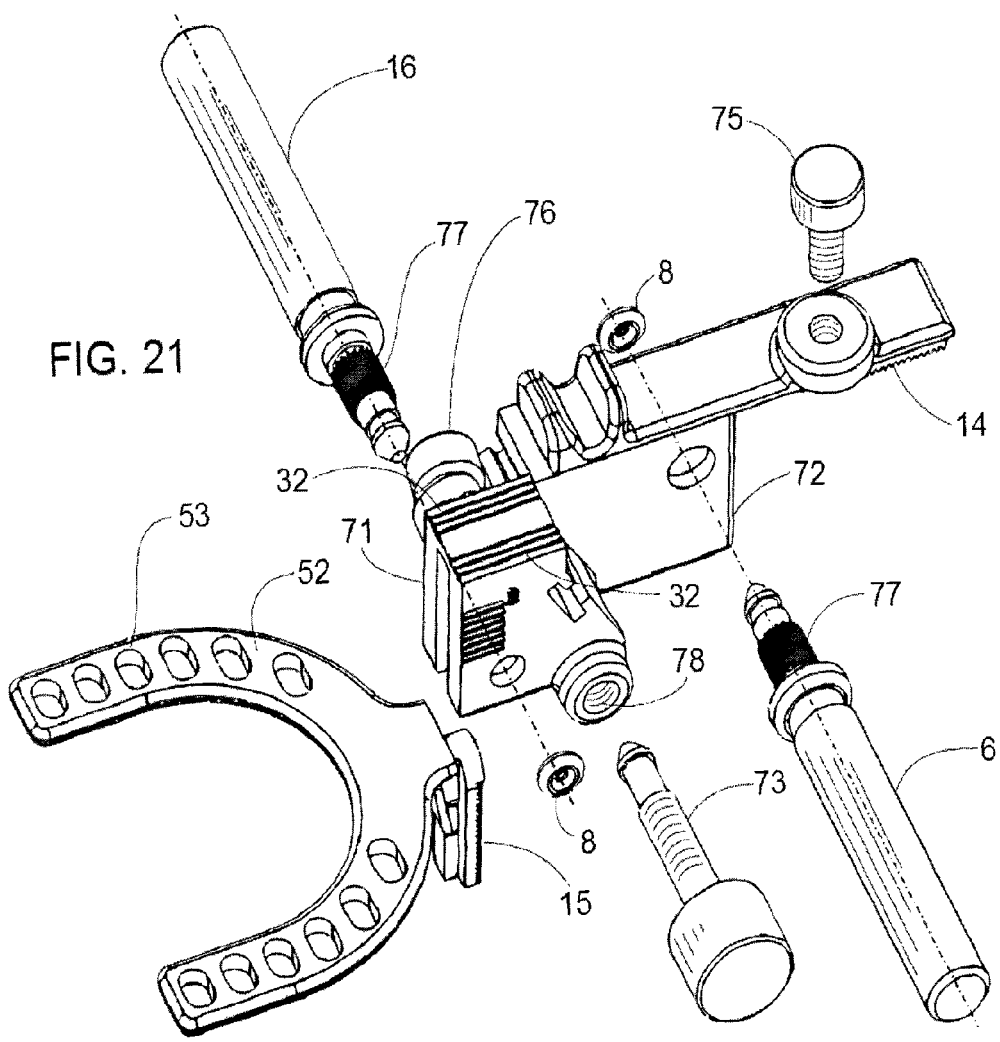
FIG. 21 is an exploded view of the embodiment of FIG. 16.

FIG. 21 shows the exploded view of the mandibular manipulator for taking a patient's measurement in 3 orthogonal axes. As described earlier, incisor pull 11 shown with the arch bite, can have bite paste applied to surface 52 and holes 53 by a physician or dentist or other health care worker to create a precisely located bite registration.

Figure 22:
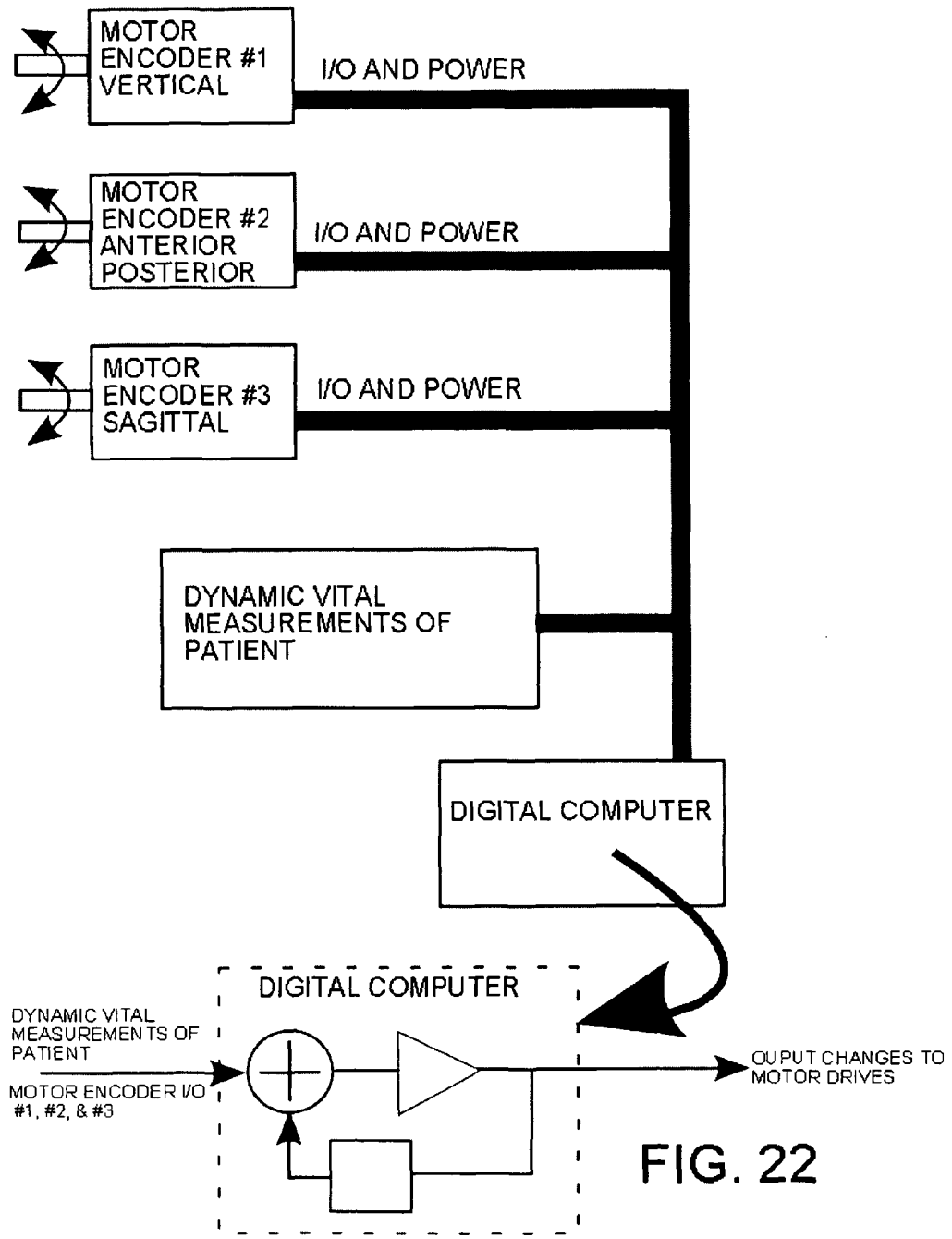
FIG. 22 is a block diagram of the manipulator driven by digital computer.

FIG. 22 shows an automated means of operating the invention by a personal computer and software. Real Time physical information of the patient is mixed with encoder information from the mandibular manipulators motor drives. These inputs are then analyzed by digital computer software to optimize the motor positioning creating the ideal mandible position for the patient. The positions can then be recorded and used as part of a bite registration method or to indicate a prescribed outcome for the patient by the physician or dentist.

As previously described, the current state of the art for manipulating a patients mandible includes the well-known George Gauge™. The George Gauge™ allows for the movement of the lower mandible only in the anteroposterior axis and minimal vertical change, whereas the instant device measures the vertical distance of the mandible as well as the anteroposterior distance of the mandible, and the relative sagittal location, all relative to the maxilla. However, while Leal and Halstrom (see, for example, U.S. Pat. No. 7,448, 388) both utilize a means of using two bite register plates, neither can be adjusted in real time using any diagnostic instruments.

In a particular embodiment, the invention includes a mandibular manipulator for manipulating a patient's jaw in a precise way, the mandibular manipulator having a connecting frame 18 comprising a piece with apertures and slots 2, 3 therein to allow first and second sliding incisor pulls (or cradles 10, 11) and first and second rotational members or knobs 6, 16 associated with each of the first and second sliding incisor pulls, respectively, to be moved independently of one another with respect to the connecting frame in order to manipulate the patient's jaw in a precise way. Each of the sliding incisor pulls has an associatable sliding member for interaction with the connecting frame at a slot and a cradle member associated with the sliding incisor pulls shaped to engage the patient's teeth and/or gums for manipulation of the jaw. Further, each rotational member is associated with the connecting frame at an aperture, and comprises a member or portion in physical contact with the associated sliding incisor pull at an interface therewith so as to change rotational motion of the rotational member to linear motion of the sliding incisor pulls and thus adjust each of the respective sliding incisor pulls with respect to the connecting frame and the patient's jaw and thus manipulate the jaw in longitudinal and vertical manners with respect to the patient's mouth; and horizontal and vertical gradation indicators (or markings or other indicia), associated with the connecting frame, for measuring relative movement of the sliding incisor pulls with respect to the connecting frame caused by rotating the first and second rotational members and utilizing the mandibular manipulator.

Preferably, such a device further has a mouthpiece having a cylindrical end 43 thereon that provides an air passageway for the patient and a closing cap at the air passageway that can form an acoustic seal, the mouthpiece having apertures 41, 42 therethrough through which the first and second rotational members extend therefrom in an acoustically sealed manner around the rotational members to create acoustic seal 44; the resilient mouthpiece further having bites 51, 52 with holes 53 to receive bite registration paste.

In developing the disclosed device, a period of methodical process was undertaken with varying instruments. The first instrument was a telescoping circular tube within a circular tube with similar shaped incisor pulls that are in the described invention. This early instrument connected the upper incisor pull to a rotating cam and the center tube provided a means of rotation for providing the vertical motion (see photograph 1). Two drawbacks of this first instrument were that it could not be used in real time with a pharyngometer mouthpiece and the rotation of the upper incisor pull to create the vertical motion also created a side load that prevented the mandible and maxilla to stay central to one another. The anteroposterior manipulation of the mandible proved successful with this first instrument.

Drawbacks to a second instrument were a slipping fit problem between the pinch wheels and incisor pulls for translating rotational motion to linear motion. The pinion handles were also too long preventing its installation in the snorkel-like mouthpiece after it was assembled. The incisor pulls also did not have a stop feature, 68, allowing them to come free of the frame. There were no graduated markings for visually reading the position of the incisor pulls nor was there a centering groove in the frame for positioning the instrument relative to the upper incisors.

As disclosed herein, the relative position of the incisor pulls to the O-ring pinch wheels was closed substantially to provide a near non-slip action as the pinion changes rotational motion to linear motion. Small mechanical features were added to the incisor pulls to prevent them from coming free of the frame once the pinions were assembled to the frame. And the pinions were shortened in length and provided with a feature to allow an extension handle to be added. This allows the instrument to be installed within the snorkel mouthpiece and then have the extension pieces added post assembly.

The snorkel-like mouthpiece also went through a development process. When the instrument's lower bite plate incorporates a tongue depressor, the mouthpiece can be simplified. The internal cylindrical diameter that holds the manipulator assembly has to be of the same internal diameter as the acoustic pharyngometer's acoustic waveguide to allow for accurate measurements by the pharyngometer. Although the relative distances from the teeth to the pharyngeal remain constant, the overall distances from the end of the acoustic waveguide are shifted the additional distance of the invention's lengthened mouthpiece tube versus the standard length mouthpiece that is provided by the pharyngometer's manufacturer. A relief is provided in the lower portion of the mouthpiece tube to allow the lower incisor pull to travel into the tube without interference. This relief provides a proper extension of the lower incisor pull.

The upper incisor pull allows extensions of about from 4 mm to about 7 mm from its neutral starting position while the lower incisor pull must allow extensions of from about 7 to about 11 mm from its neutral position. These distances are what is preferred by dentists and physicians for the inclusion of most patient's natural maxilla and mandible shapes and positions.

A second problem with the current state of the art is that the motion measured with a George Gauge™ can only be performed in one plane. The invention allows three planes of measurement for both dental and medical practices required of a two- or three-plane measurement. Also, the George Gauge™ cannot be used remotely for real time measurement. This is in fact due to the need to adjust anterior/posterior position in the same axis as the diagnostic instruments being used. A similar problem is encountered with the instruments by Halstrom or Leal.

This invention provides a means of moving and measuring the mandible position in real time as the patient is undergoing diagnostic procedures. The manipulation can be done by hand within the medical procedure for monitoring real time feedback from diagnostic instruments or the manipulation can be motor driven with computer feedback to obtain the ideal position. The manipulation of the mandible relative to the maxilla by the invention, allows for real time measurements to take place with repeatable precision thus decreasing diagnoses time while accurately quantifying the position of the upper and lower bite of the teeth. In this way, a dental appliance can be accurately built from the Dental Articulator as a result of the procedure. It can also allow the physician or dentist to prescribe another method to reduce the episodes of sleep apnea.

After being apprised of the instant disclosure, those of skill in the art, to the extent the components are not already commercially available, will be readily able to manufacture and assemble the components of the invention by methods that would include, e.g., machining or molding. The materials that could be utilized to create the components of the invention include materials such as metals, polycarbonate, nylon, polypropylene, delrin, and other appropriately biocompatible materials. Assembly and sizing can be as per the associated figures (see, e.g., FIGS. 15 through 17), the incorporated prior art, and may be customizable dependent upon the size of the mouth, mandible, and maxilla of the particular patient. The size of the components (e.g., knobs) can be also modified to suit the particular healthcare professional utilizing the equipment.

What is claimed is:

1. A mandibular manipulator for manipulating a patient's mandible in a precise way, the mandibular manipulator comprising:
a connecting frame comprising at least one piece with apertures and slots therein to allow a first sliding incisor pull, a second sliding incisor pull, a first rotational member associated with the first sliding incisor pull, and a second rotational member associated with the second sliding incisor pull, which first and second sliding incisor pulls move independently of one another with respect to said connecting frame,
wherein each rotational member has a slip resistant surface adapted for grabbing;
wherein each of said sliding incisor pulls comprises an associatable sliding member for interaction with said connecting frame at a slot and a cradle member associated with said sliding incisor pulls shaped to engage the patient's teeth and/or gums for manipulation of the mandible, and further wherein each said rotational member is associated with the connecting frame at an aperture, and comprises a member or portion in physical contact with the associated sliding incisor pull at an interface therewith so as to change rotational motion of the rotational member to linear motion of the sliding incisor pulls and thus adjust each said respective sliding incisor pull with respect to the connecting frame and the patient's mandible and thus manipulate the mandible in a longitudinal and vertical manner with respect to the patient's mouth; and
horizontal and vertical gradation indicators, associated with said connecting frame, for measuring relative movement of the sliding incisor pulls with respect to the connecting frame caused by rotating said first and second rotational members and utilizing said mandibular manipulator.

2. A mandibular manipulator for manipulating a patient's mouth in a precise way, the mandibular manipulator comprising:
a connecting frame comprising at least one piece with apertures and slots therein, a first sliding incisor pull, a second sliding incisor pull, a first rotational member associated with the first sliding incisor pull, and a second rotational member associated with the second sliding incisor pull, which first and second sliding incisor pulls move independently of one another with respect to the connecting frame, so as to manipulate the patient's mandible in a precise way;
wherein each of the sliding incisor pulls comprises an associatable sliding member for interaction with the connecting frame at a slot and a cradle member associated with the sliding incisor pulls shaped to engage the patient's teeth and/or gums for manipulation of the mandible, and further wherein each rotational member is associated with the connecting frame at an aperture, and comprises a member or portion in physical contact with the associated sliding incisor pull at an interface therewith so as to change rotational motion of the rotational member to linear motion of the respective sliding incisor pull and thus adjust the respective sliding incisor pull with respect to the connecting frame and the patient's mandible and thus manipulate the mandible in a longitudinal and vertical manner with respect to the patient's mouth;
horizontal and vertical gradation indicators, associated with the connecting frame, for measuring relative movement of the sliding incisor pulls with respect to the connecting frame caused by rotating the first and second rotational members and utilizing the mandibular manipulator; and
a mouthpiece having a cylindrical end thereon that provides an air passageway for the patient and a closing cap at the air passageway that can form an acoustic seal, said mouthpiece having apertures therethrough, through which the first and second rotational members extend therefrom in an acoustically sealed manner around the rotational members.

3. The mandibular manipulator of claim 1, further comprising a third rotational member for sagittal movement of the mandible.

4. The mandibular manipulator of claim 3, further having sagittal gradation indicators for measuring sagittal movement of the mandible caused by manipulating the third rotational member of the mandibular manipulator.

5. The mandibular manipulator of claim 4, wherein the horizontal, vertical, and sagittal gradation indicators are not applied to said first rotational member, second rotational member, or third rotational member.

6. The mandibular manipulator of claim 1, wherein each rotational member has a flange adapted to engage a stationary protruding surface and create a soft detent of the rotation.

7. A mandibular manipulator for manipulating a patient's mandible in a precise way, the mandibular manipulator comprising:
a connecting frame comprising at least one piece with apertures and slots therein, a first sliding incisor pull, a second sliding incisor pull, a first rotational member associated with the first sliding incisor pull, and a second rotational member associated with the second sliding incisor pull wherein at least one rotational member is associated with the connecting frame by use of a resilient circular ring, which first and second sliding incisor pulls move independently of one another with respect to the connecting frame, so as to manipulate the patient's mandible in a precise way;
wherein each of the sliding incisor pulls comprises an associatable sliding member for interaction with the connecting frame at a slot and a cradle member associated with the sliding incisor pulls shaped to engage the patient's teeth and/or gums for manipulation of the mandible, and further wherein each rotational member is associated with the connecting frame at an aperture, and comprises a member or portion in physical contact with the associated sliding incisor pull at an interface therewith so as to change rotational motion of the rotational member to linear motion of the respective sliding incisor pull and thus adjust the respective sliding incisor pull with respect to the connecting frame and the patient's mandible and thus manipulate the mandible in a longitudinal and vertical manner with respect to the patient's mouth; and
horizontal and vertical gradation indicators, associated with the connecting frame, for measuring relative movement of the sliding incisor pulls with respect to the connecting frame caused by rotating the first and second rotational members and utilizing the mandibular manipulator.

8. The mandibular manipulator of claim 7, wherein the resilient circular ring creates an axial bias of the rotational member.

9. The mandibular manipulator of claim 1, wherein at least one rotational member is threaded for association with a corresponding threaded receptacle in the connecting frame.

10. The mandibular manipulator of claim 1, wherein at least one of the sliding members has arched plates physically associated therewith, said arched plates having apertures therethrough for receiving bite registration material.

11. A mandibular manipulator for manipulating a patient's mandible in a precise way, the mandibular manipulator comprising:

a connecting frame comprising at least one piece with apertures and slots therein, a first sliding incisor pull, a second sliding incisor pull, a first rotational member associated with the first sliding incisor pull, and a second rotational member associated with the second sliding incisor pull, which first and second sliding incisor pulls move independently of one another with respect to the connecting frame, so as to manipulate the patient's mandible in a precise way;

wherein each of the sliding incisor pulls comprises an associatable sliding member for interaction with the connecting frame at a slot and a cradle member associated with the sliding incisor pulls shaped to engage the patient's teeth and/or gums for manipulation of the mandible, wherein at least one of the sliding members has a member or portion for depressing the patient's tongue, and further wherein each rotational member is associated with the connecting frame at an aperture, and comprises a member or portion in physical contact with the associated sliding incisor pull at an interface therewith so as to change rotational motion of the rotational member to linear motion of the respective sliding incisor pull and thus adjust the respective sliding incisor pull with respect to the connecting frame and the patient's mandible and thus manipulate the mandible in a longitudinal and vertical manner with respect to the patient's mouth; and horizontal and vertical gradation indicators, associated with the connecting frame, for measuring relative movement of the sliding incisor pulls with respect to the connecting frame caused by rotating the first and second rotational members and utilizing the mandibular manipulator.

12. The mandibular manipulator of claim 2, wherein at least one rotational member is motorized.

13. The mandibular manipulator of claim 12, wherein the at least one rotational member that is motorized is controlled by computer software.

14. A mandibular manipulator for manipulating a patient's mandible in a precise way, the mandibular manipulator comprising:

a connecting frame comprising at least one piece with apertures and slots therein, a first sliding incisor pull, a second sliding incisor pull, a first rotational member associated with the first sliding incisor pull, and a second rotational member associated with the second sliding incisor pull, which first and second sliding incisor pulls move independently of one another with respect to the connecting frame, so as to manipulate the patient's mandible in a precise way;

wherein each of the sliding incisor pulls comprises an associatable sliding member for interaction with the connecting frame at a slot and a cradle member associated with the sliding incisor pulls shaped to engage the patient's teeth and/or gums for manipulation of the mandible, and further wherein each rotational member is associated with the connecting frame at an aperture, and comprises a member or portion in physical contact with the associated sliding incisor pull at an interface therewith so as to change rotational motion of the rotational member to linear motion of the respective sliding incisor pull and thus adjust the respective sliding incisor pull with respect to the connecting frame and the patient's mandible and thus manipulate the mandible in a longitudinal and vertical manner with respect to the patient's mouth;

horizontal and vertical gradation indicators, associated with the connecting frame, for measuring relative movement of the sliding incisor pulls with respect to the connecting frame caused by rotating the first and second rotational members and utilizing the mandibular manipulator; and wherein each sliding incisor pull is adapted to have a self-capturing element to prevent the sliding incisor pulls from unintentionally disassembling from the mandibular manipulator.

15. A mandibular manipulator comprising:

a connecting frame comprising at least one piece with apertures and slots therein, a first sliding incisor pull, a second sliding incisor pull, a first rotational member associated with the first sliding incisor pull, and a second rotational member associated with the second sliding incisor pull, which first and second sliding incisor pulls move independently of one another with respect to the connecting frame;

wherein each of the sliding incisor pulls comprises an associatable sliding member for interaction with the connecting frame at a slot and a cradle member associated with the sliding incisor pulls shaped to engage a patient's teeth and/or gums for manipulation of the mandible, and further wherein each rotational member is associated with the connecting frame at an aperture, and comprises a member or portion in physical contact with the associated sliding incisor pull at an interface therewith so as to change rotational motion of the rotational member to linear motion of the respective sliding incisor pull and thus adjust the respective sliding incisor pull with respect to the connecting frame and the patient's mandible and thus manipulate the mandible in a longitudinal and vertical manner with respect to the patient's mouth;

horizontal and vertical gradation indicators, associated with the connecting frame, for measuring relative movement of the sliding incisor pulls with respect to the connecting frame caused by rotating the first and second rotational members and utilizing the mandibular manipulator; and an acoustic oral pharyngometer associated with the mandibular manipulator.

* * * * *